United States Patent [19]

Bordow

[11] 4,240,433

[45] Dec. 23, 1980

[54] FLUID ASPIRATION DEVICE AND TECHNIQUE FOR REDUCING THE RISK OF COMPLICATIONS

[76] Inventor: Richard A. Bordow, 6114 Terryhill Dr., La Jolla, Calif. 92037

[21] Appl. No.: 818,016

[22] Filed: Jul. 22, 1977

[51] Int. Cl.³ .................... A61B 17/34; A61M 1/00
[52] U.S. Cl. .................... 128/347; 128/276
[58] Field of Search .............. 128/276, 277, 278, 347, 128/348, 349 B, 349 BV, 350, 246, 221, 214.4, 6, 4; 27/24 A

[56] References Cited

U.S. PATENT DOCUMENTS

| | | | |
|---|---|---|---|
| 1,087,845 | 2/1914 | Stevens | 128/221 |
| 1,248,492 | 12/1917 | Hill | 128/347 |
| 1,922,084 | 4/1931 | Gerow | 128/349 |
| 2,001,638 | 5/1935 | Tornsjo | 128/347 |
| 2,919,697 | 1/1960 | Kim | 128/349 |
| 3,417,745 | 12/1968 | Sheldon | 128/6 |
| 3,438,375 | 4/1969 | Ericson | 128/349 |
| 3,509,884 | 9/1967 | Bell | 128/350 |
| 3,662,754 | 5/1972 | Halloran | 128/221 |
| 3,703,899 | 11/1972 | Calinog | 128/347 |
| 3,746,003 | 7/1973 | Blake et al. | 128/349 B |
| 3,777,757 | 12/1973 | Gray et al. | 128/278 |
| 3,799,173 | 3/1974 | Kamen | 128/349 |
| 3,833,003 | 9/1974 | Taricco | 128/347 |
| 3,952,742 | 4/1976 | Taylor | 128/347 |
| 3,954,110 | 5/1976 | Hutchison | 128/349 B |
| 3,982,546 | 9/1976 | Friend | 128/350 |
| 3,995,619 | 12/1976 | Glatzer | 128/2 B |
| 4,014,333 | 3/1977 | McIntyre | 128/276 |

FOREIGN PATENT DOCUMENTS

| | | | |
|---|---|---|---|
| 320387 | 12/1902 | France | 128/276 |
| 320387 | 5/1903 | France | 128/276 |
| 832992 | 10/1938 | France | 128/303 R |
| 368151 | 6/1974 | Sweden | 128/2 A |
| 226791 | 1/1969 | U.S.S.R. | 128/278 |

*Primary Examiner*—Robert W. Michell
*Assistant Examiner*—Arthur S. Rose
*Attorney, Agent, or Firm*—Saidman & Sterne

[57] ABSTRACT

A device and technique utilized in body fluid aspiration which minimizes the risk of complications that normally may result from accidental puncture of internal organs. The device includes a sharp-tipped fluid aspiration needle which features cushioning means, preferably in the form of an inflatable balloon, positionable between the sharp tip of the needle and the internal organs during the aspiration procedure. The inflatable balloon is preferably connected to an end of a cannula which is, in turn, slidably positionable within the hollow needle. The cannula is in a retracted position in the needle upon insertion of the latter through the body. When the fluid is located, the cannula is advanced to a locked position beyond the sharp tip of the needle, whereupon the balloon is inflated and the fluid aspiration commenced. The inflated balloon and extended cannula ablate the sharp edge of the needle as well as minimize movement thereof during the procedure to substantially reduce the risk of accidental puncture.

15 Claims, 5 Drawing Figures

U.S. Patent    Dec. 23, 1980    4,240,433
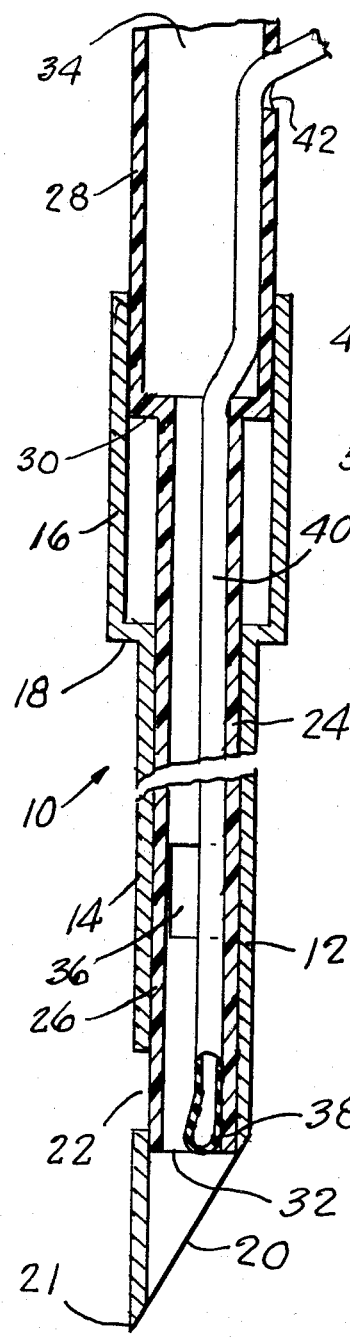
FIG. 1.
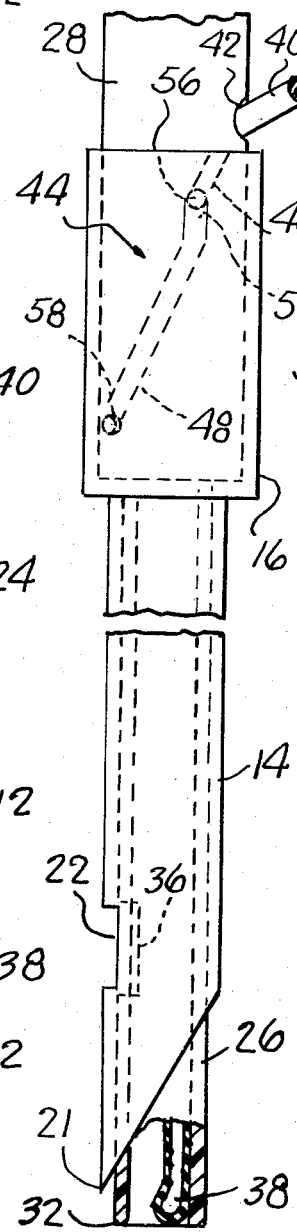
FIG. 2.
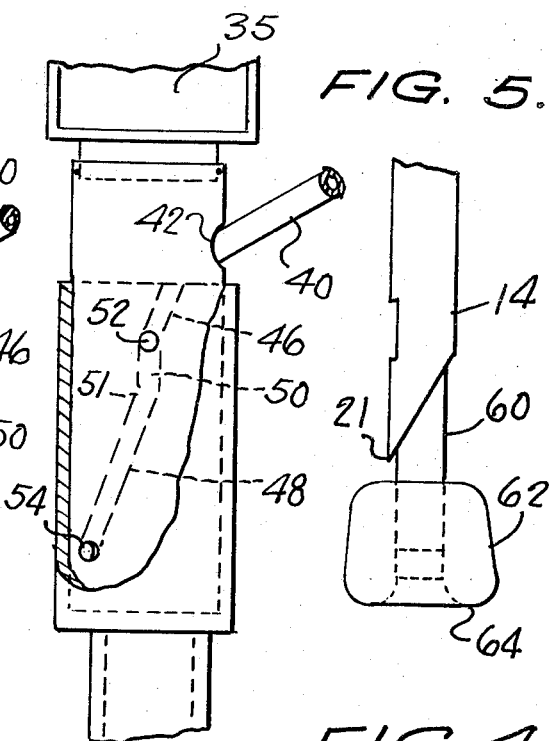
FIG. 5.
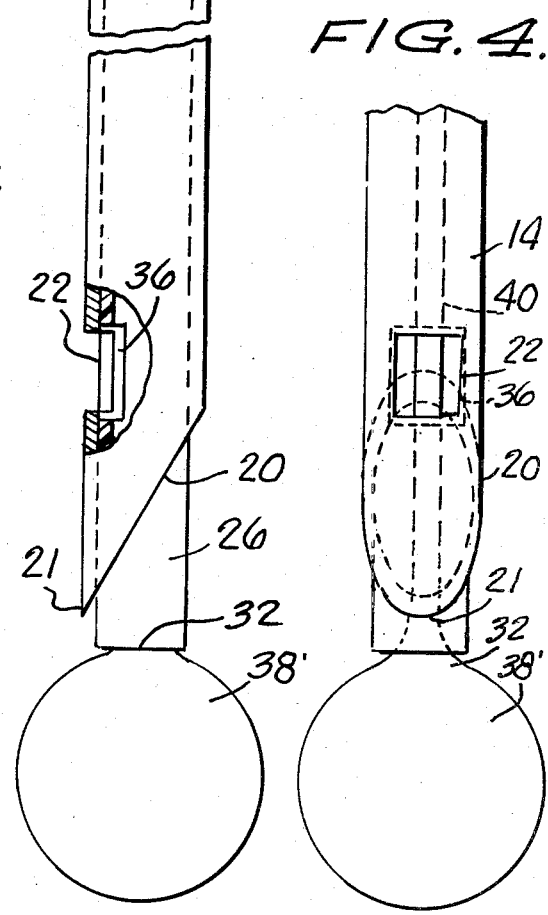
FIG. 4.
FIG. 3.

FLUID ASPIRATION DEVICE AND TECHNIQUE FOR REDUCING THE RISK OF COMPLICATIONS

BACKGROUND OF THE INVENTION

1. Field of the Invention

The present invention is related to body fluid aspiration devices and techniques and, more particularly, is directed towards a body fluid aspiration device and technique which substantially reduces the risk of complications resulting from accidental puncture of the internal organs in the vicinity of the body fluid to be aspirated.

2. Description of the Prior Art

There are many common medical procedures which require fluids to be withdrawn from the body.

Fluid accumulation occurs abnormally in many pathologic situations and its removal may be accomplished as part of a diagnostic evaluation or as a form of therapy. The most common examples of the former are fluid forming around the lung, intestines and heart. The most common reasons for a therapeutic fluid removal would be as a result of pressure build-up of fluid around certain organs which would cause specific organ dysfunction syndromes. It is possible, in fact, to accumulate several liters of fluid in such areas.

A thoracentesis is the procedure for removal of fluid around the lungs. Other procedures are known, such as a paracentesis (withdraw of fluid from the abdomen), or a pericardiocentesis (withdrawl of fluid around the heart).

In a thoracentesis procedure, for example, a hollow needle is inserted through the chest wall. A syringe is connected to the end of the needle, usually via a three-way stop-cock valve. When the fluid mass is located, the fluid is aspirated into the syringe with the valve in a first position. Once the syringe is filled, the valve is switched and fluid is ejected from the syringe into a stand-by receptacle. This procedure is repeated until all of the fluid has been withdrawn, whereafter the needle is removed from the cavity.

The thoracentesis procedure is unfortunately accompanied by a significant risk of a complication known as pneumothorax. A pneumothorax is a collapsed lung which results from lung puncture and associated leakage of air into the pleural space with equalization of atmospheric and intrapleural pressure. Intrapulmonary hemorrhage may also result from accidental puncture of intrapulmonary blood vessels. In a thoracentesis there is also a smaller, but equally undesirable, risk of visceral (liver and spleen) puncture with subsequent intraorgan bleeding and death.

In a thoracentesis, the actual time of the lung or visceral puncture is unknown, although there are three distinct possibilities. The puncture could occur at the time of entry of the needle into the chest; however, this is unlikely if fluid is present since there is a reasonable distance to the lung parenchyma. A second possibility is that the puncture could occur while fluid is being aspirated from within the pleural space; this is more likely since it is frequently difficult to stabilize the needle and prevent to and fro movement which may accidentally push the needle into the visceral organ. Finally, the puncture could occur at the end of the procedure; this is highly likely since, at that time, there is only a small amount of fluid remaining and the lung parenchyma is closest to the tip of the needle.

The same types of risks occur, with respect to other internal organs, during a paracentesis, pericardiocentesis, and other body fluid aspiration procedures.

U.S. Pat. No. 3,982,546 evidences an improved body fluid draining device wherein, after the hollow needle is inserted into the body cavity to be drained, a flexible plastic cannula is positioned through the needle into the cavity whereafter the outer needle is withdrawn. The plastic cannula is connected to a syringe or other fluid withdrawal device. While providing an improvement over prior techniques, use of this device nevertheless has several drawbacks. For example, an inexperienced operator may accidentally attempt to withdraw the plastic cannula before the needle is withdrawn. Due to the fact that the plastic cannula when fully inserted extends appreciably beyond the tip of the needle, premature withdrawal of same can sever the cannula within the cavity which can, in turn, require surgery to remove the severed portion. Additionally, the tip of the plastic cannula, while not as sharp as the needle point, is nevertheless sufficiently hard to damage the lung or other organs if improperly used.

U.S. Pat. No. 3,777,757 to Gray et al teach a sucking wound plug and chest aspirator which includes a catheter for placement through a chest wound and includes an inflatable bag which, upon inflation, is intended to fit snugly within the edges of the chest wall which define the perforation. The terminal distal end of the catheter is provided with a cushioning means for preventing damage to any delicate internal organs.

I am aware of many different types of balloon catheters utilized in various medical procedures. For example, a Fogarty catheter employs a balloon to extricate clots from the vascular beds. Another familiar use of a balloon catheter is as a retention device for retaining a tube in, for example, the bladder. Endotracheal devices frequently use a balloon to surround a rather rigid plastic tube to prevent necrosis of the airway. A Swan-Ganz catheter is also known and is used in cardiac catherization. It has a balloon around a plastic catheter to protect the heart muscle from being irritated by the plastic catheter and to facilitate movement of the catheter into a predetermined location to obtain pressure measurements.

Prior art United States patents of which I am aware which exemplify the above-referenced state of the art include U.S. Pat. Nos. 3,799,173; 3,954,110; 3,438,375; 1,922,084; 3,703,899; 3,833,003; 3,952,742; 3,448,739; 3,634,924; and 3,746,003.

OBJECTS AND SUMMARY OF THE INVENTION

It is therefore a primary object of the present invention to provide a method and apparatus for minimizing the risk of puncture of internal organs during a body fluid aspiration procedure.

Another object of the present invention is to provide an apparatus for use in connection with aspiration of fluids from a body cavity which includes means for ablating the sharp point of the insertion needle.

An additional object of the present invention is to provide a technique for aspirating fluid from the body which utilizes a hollow needle having a sharp tip and means for substantially reducing the risk of puncture of the visceral organs by the sharp tip.

A still further object of the present invention is to provide a method and apparatus for use in body fluid aspiration which is inexpensive, easy to manufacture, may be assembled from readily available components, and thereby be made available on a wide basis as an inexpensive means for reducing risk of complications from aspiration procedures.

The foregoing and other objects are attained in accordance with one aspect of the present invention through the provision of apparatus for aspirating fluid from a body cavity, which comprises needle means having a sharp tip for facilitating entry to the body cavity, cannula means movably disposed within the needle means, and means connected to the cannula means for reducing the risk of puncture of internal organs by the sharp tip of the needle means. The risk-reducing means in a preferred form comprises a selectively inflatable balloon which, upon inflation, becomes positioned between the sharp tip and the internal organs for protecting the latter from the former. In a preferred embodiment, the needle means is substantially hollow and includes a first fluid intake port positioned in the side wall thereof, while the cannula means is also hollow and includes a second fluid intake port positioned in its side wall. Means are further provided for positioning the cannula means from a first position within the needle means to a second position projecting beyond the tip of the needle means. The second position is further defined by the registry of the first and second fluid intake ports for the purposes of aspirating fluid therethrough. Means are also preferably provided for fixing the cannula means and needle means in the second position to minimize movement during the procedure. A syringe or like means is connected to the distal end of the cannula means for withdrawing the fluid, and a conduit means extends through the cannula for permitting inflation of the balloon.

In accordance with other aspects of the present invention, a method is provided for reducing the risk of puncture of internal organs during a medical procedure for aspirating fluid from a body cavity, which comprises the steps of inserting a hollow needle having a sharp tip into the body cavity, and positioning a cannula through the hollow needle so that end thereof extends beyond the tip of the needle into the cavity. Finally, the method includes the step of inflating a balloon connected to the extended end of the cannula whereby the inflated balloon is positioned between the sharp tip of the needle and the internal organs surrounding the cavity. The method may further comprise the step of aligning a pair of fluid intake ports formed in the needle and the cannula, respectively, when the cannula is positioned to extend beyond the tip of the needle. The technique may still further include the step of locking the position of the cannula relative to the needle when the end of the cannula extends beyond the tip of the needle in its fluid aspirating position.

In accordance with still other aspects of the present invention, I have provided apparatus which comprises a hollow needle having a sharp tip, conduit means movably disposed within the hollow needle, and an inflatable balloon connected to the conduit means so as to be movable therewith from a position within the hollow needle to a position beyond the needle tip. The conduit means may include means for inflating the balloon which may, in turn, extend within the conduit means. The balloon may be positioned on the outer periphery of one end of the conduit means, or alternatively may be positioned within one end of the conduit means prior to inflation thereof.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 1 is a longitudinal, sectional view, partially broken, illustrating a preferred embodiment of the present invention;

FIG. 2 is a side, partially broken and sectional view of the preferred embodiment illustrated in FIG. 1 but in an alternative operating position;

FIG. 3 is a view of the preferred embodiment of the present invention similar to that illustrated in FIG. 2 in another operative condition;

FIG. 4 is a side view of a portion of the components of the present invention illustrated in FIG. 3; and FIG. 5 is a side view of an alternative embodiment of the present invention.

DETAILED DESCRIPTION OF THE PREFERRED EMBODIMENTS

Referring now to the drawings, wherein like reference numerals represent identical or corresponding parts throughout the several views, and more particularly to FIG. 1 thereof, a preferred embodiment of the fluid aspiration device of the present invention is indicated generally by reference numeral 10.

Fluid aspiration device 10 comprises an outer, hollow needle 12, which is preferably formed of metal and therefore may be sterilized so as to be reuseable, if desired. Needle 12 comprises an elongated, constant diameter main body portion 14 and an increased diameter rear portion 16. Main body portion 14 and rear portion 16 are interconnected by a transverse annular rim 18.

The lower end of main body portion 14 of needle 12 terminates in an open end 20, which may be beveled as is customary to facilitate insertion. The lowermost tip of the needle point 20 is indicated by reference numeral 21. Positioned in the main body portion 14 of needle 12 somewhat rearwardly of tip 21 is a fluid intake port 22.

Disposed within the hollow needle 12 is a movable cannula 24, preferably comprised of plastic, whose shape is substantially congruent to that of the metallic needle 12. Cannula 24 includes an elongated main body portion 26 whose external diameter is preferably sized so as to be slidably receivable within the internal diameter of the main body portion 14 of needle 12.

The cannula 24 further includes an increased diameter rear portion 28 which is interconnected with the main body portion 26 by a transverse rim or flange 30.

The lower end 32 of cannula 24 is open, while the distal end 34 thereof is also in open fluid communication with either a conventional syringe 35 (FIG. 3) or, alternatively, to a standard three-way stop cock valve. Positioned somewhat rearwardly of open end 32 and formed in the main body portion 26 is a fluid intake port 36, of the same general dimensions as fluid intake port 22 of needle 12.

Positioned near the lower end of main body portion 26 of inner cannula 24 is an inflatable balloon or bag 38 which is indicated in FIGS. 1 and 2 in its deflated state. Balloon 38 may be inflated by means of an air conduit or lumen 40 which extends lengthwise through the plastic inner cannula 24 to an aperture 42 formed in the increased diameter portion 28 thereof. Lumen 40 may be secured to the inner wall of cannula 24 by any conventional means. Alternatively, the cannula 24 and lumen 40 may be formed of extruded plastics, or any other suitable material. The balloon 38 may be positioned as illustrated internally of the open end 32 of cannula 24 or, alternatively, may be positioned externally thereof, as will be explained in greater detail hereinafter with respect to the alternative embodiment illustrated in FIG. 5.

Referring now more particularly to FIGS. 2 and 3, the inner wall of the increased diameter portion 16 of needle 12 includes an irregular, generally S-shaped track indicated generally by reference numeral 44. Track 44 comprises a pair of spiral portions 46 and 48 which are interconnected via a straight portion 50. As seen in FIG. 3, a pair of locking recesses 52 and 54 are positioned on the innner wall of portion 16 at the terminal ends of spiral tracks 46 and 48, respectively, for a purpose which will become more clear hereinafter.

The outer wall of the increased diameter portion 28 of the inner plastic cannula 24 includes a pair of projections 56 and 58 which are sized so as to slidably fit within track 44 as well as to be lockingly engaged by recesses 52 and 54. Accordingly, track 44 serves as a guide for the projections 56 and 58, and recesses 52 and 54 serve as means for locking the plastic cannula 24, against rotation as well as axial movement, with respect to outer needle 12.

The technique of the present invention may be better understood from the following description of the mode of utilizing the device of the present invention. In operation, before inserting the fluid aspiration device 10 through the body, the plastic cannula 24 is positioned within needle 12 such that the forwardmost projection 58 enters spiral portion 46 of track 44. The cannula is then rotated to advance projection 58 along the spiral portion 46, and is then advanced axially until projection 58 reaches the entrance to spiral portion 48 as indicated by the dotted outline 51 in FIG. 3. At position 51 may be formed a slight depression in track 44 to temporarily fix the position of cannula 24 with respect to needle 12. At this point, the components are preferably in the relative position indicated in FIG. 1, and the needle 12 is ready to be inserted into the patient.

The tip 21 of the needle is then inserted through the chest of the patient (in a thoracentesis), and the syringe 35 is continually operated until fluid is drawn through open ends 20 and 32 of needle 12 and cannula 24, respectively. When fluid is initially detected in the syringe 35, it is an indication that fluid mass has been located. Note that during this initial aspiration, fluid intake ports 22 and 36 are out of registry with one another and are also blocked by the respective main body portions 26 and 14 of the cannula 24 and needle 12 (see FIG. 1).

When the fluid body is located as evidenced by fluid in the syringe 35, the cannula 24 is again rotated so as to advance forward projection 58 along spiral portion 48 of track 44 until it reaches the recess 54. During the travel of projection 58 in track 48, the upper projection 56 will enter spiral portion 46. Projections 56 and 58 are spaced so as to lock within recesses 52 and 54 at substantially the same time, whereupon the cannula 24 and needle 12 will be in the relative positions illustrated in FIG. 2. Note that the end 32 of cannula 24 extends appreciably beyond the tip 21 of needle 12 so as to ablate the sharp cutting edge thereof. This also serves to bring the inflatable balloon or bag 38 into position for inflation. Further, port 36 of cannula 24 has been advanced axially and rotatingly so as to come into registry with port 22 of needle 12.

With the cannula 24 and needle 12 in the position illustrated in FIG. 2, the balloon 38 is inflated via lumen 40 to the operative position illustrated in FIG. 3. The inflated balloon 38' serves as a soft, yet effective barrier between the adjacent internal body organ, e.g. a lung, and the needle tip 21 so as to substantially reduce the risk of puncture. Aspiration may be continued by means of syringe 35 or the like via aligned ports 22 and 36.

The relative locking of the needle 12 and cannula 24 reduces the chances of slippage of the inserted cannula back and forth during the procedure, thus reducing the chance of balloon puncture. Further, the inflated bag 38', along with the plastic end 32 of the cannula 24, serve as an effective barrier between the needle point 21 and the adjacent vital organs at the critical period near the end of the aspiration procedure when nearly all the fluid has been emptied from the body cavity and the risk of puncture is greatest. Clearly, the particular locking means described and illustrated is only by way of example, as many different but equivalent constructions will be obvious to a person of ordinary skill in this art.

FIG. 5 illustrates an alternative manner of providing a balloon-like inflatable bag 62 on the outer peripheral surface of a cannula 60 so as to serve the same function as the first embodiment. In FIG. 5, the end 64 of balloon 62, when inflated, extends beyond the end of the cannula 60, and forms a donut-like annulus in an end view. The balloon 62 and cannula 60 of FIG. 5 may be constructed, for example, in accordance with U.S. Pat. No. 3,746,003. Clearly, other equivalent constructions will suggest themselves to a person of ordinary skill in the art.

Obviously, therefore, numerous modifications and variations of the present invention are possible in light of the above teachings. It is therefore to be understood that within the scope of the appended claims, the invention may be practiced otherwise than as specifically described herein.

I claim as my invention:

1. Apparatus for aspirating fluid from a body cavity, which comprises:
   elongated substantially hollow needle means having a sharp tip at one end thereof for facilitating entry to a body cavity;
   elongated substantially hollow cannula means being movably disposed within said needle means, said needle means having an opening at said one end sized such that said cannula means may be slid through said opening;
   selectively inflatable balloon means connected to said cannula means so as to be positionable, upon inflation, between said tip and internal organs near said cavity for reducing the risk of puncture of said internal organs by said tip;
   a first fluid intake port in the wall of said needle means spaced from said opening; and
   a second fluid intake port positioned in the wall of said cannula means so as to be registrable with said first fluid intake port to permit flow therethrough.

2. The apparatus as set forth in claim 1, further comprising means for positioning said cannula means from a first position within said needle means to a second position projecting slightly beyond said tip of said needle means, said second position further defined by the registry of said first and second fluid intake ports.

3. The apparatus as set forth in claim 2, further comprising means for fixing said cannula means and said needle means in said second position.

4. The apparatus as set forth in claim 3, further comprising means connected to the distal end of said cannula means for withdrawing fluid therethrough.

5. The apparatus as set forth in claim 1, further comprising conduit means extending through said cannula means for permitting inflation of said balloon.

6. The apparatus as set forth in claim 1, wherein said cannula means further includes an open end positioned in use adjacent said tip.

7. The apparatus as set forth in claim 6, wherein said open end comprises a third fluid inlet port to which said organ puncture risk reducing means is connected.

8. A method of reducing the risk of puncture of internal organs during a medical procedure for aspirating fluid from a body cavity, which comprises the steps of:
 inserting a hollow needle having an opening with a sharp tip into said body cavity, said needle having a fluid intake port in the wall thereof spaced from said opening;
 positioning a cannula through the hollow needle so that an end thereof extends through said opening of said tip of said needle into said cavity;
 inflating a balloon connected to said end of said cannula whereby said inflated balloon is positioned between said tip and said internal organs; and
 aligning a fluid intake port formed in the wall of said cannula with said fluid intake port of said needle when said cannula is positioned to extend beyond the tip of said needle.

9. The method as set forth in claim 8, further comprising the step of locking the position of said cannula relative to said needle when said end of said cannula extends beyond said tip of said needle.

10. Apparatus, which comprises:
 a hollow needle having an opening with a sharp tip and a first aperture spaced from said opening formed in the wall thereof;
 conduit means movably disposed within said hollow needle and having a second aperture formed in the wall thereof, said first aperture being registrable with said second aperture;
 an inflatable balloon connected within one end of said conduit means so as to be movable therewith from a position within said hollow needle to a position beyond said needle tip;
 means positioned within said conduit means for inflating said balloon; and
 means comprising said first and second apertures for aspirating fluid through said needle and said conduit means after said balloon is inflated.

11. Apparatus, which comprises means for aspirating fluid from a body cavity in an area adjacent an internal organ, which includes:
 a hollow needle having a side wall, a first port in said side wall and a sharp tip defining an opening at one end thereof for entering the body, said first port being spaced from said opening;
 a cannula having a side wall with a second port formed therein, said cannula movable axially within said needle from a first position inside said needle to a second position extending beyond said tip, said first and second ports being aligned in said second position;
 said cannula having inflatable balloon means movable therewith for reducing the risk of accidental puncture of said organ by said tip during the aspiration of fluid from said cavity through said aligned ports.

12. The apparatus as set forth in claim 11, wherein said balloon means is positioned on the outer periphery of one end of said cannula.

13. The apparatus as set forth in claim 11, wherein said balloon means is positioned within one end of said cannula prior to inflation.

14. A method of reducing the risk of puncture of an internal organ during a medical procedure for aspirating fluid from a body cavity positioned near said organ, which comprises the steps of:
 positioning hollow needle means having an open tip and an apertured wall spaced from said tip into said body cavity;
 positioning conduit means having an apertured wall through said needle means so that an end thereof extends through said open tip of said needle means into said cavity;
 reducing the risk of puncture of said organ by said tip of said needle means by inflating balloon means connected to said end of said conduit means whereby said balloon means will be positioned between said tip and said internal organ; and
 aligning the apertures in said apertured walls of said hollow needle means and said conduit means for aspirating fluid therethrough.

15. Apparatus, which comprises:
 first means having a wall and a sharp open tip for entering the body and a first fluid intake port located in said wall thereof spaced from said open tip;
 second means for carrying fluid and having a free end and a second fluid intake port located in a wall thereof and rearwardly spaced from said free end, said second means movable axially within said first means from a withdrawn position where said free end is spaced rearwardly of said tip and where said first and second intake ports are not aligned, to an extended position where said free end extends forwardly of said tip and said first and second intake ports are aligned for permitting fluid flow therethrough; and
 inflatable balloon means connected to and movable with said free end of said second means for reducing the risk of puncture by said sharp tip, wherein said free end forms port means for aspirating fluid through said second means prior to the inflation of said balloon means.

* * * * *